United States Patent [19]

Grice et al.

[11] Patent Number: 4,914,072
[45] Date of Patent: Apr. 3, 1990

[54] PHOSPHORUS/TITANIA/ZIRCONIA CATALYST FOR PREPARATION OF LINEAR POLYETHYLENEPOLYAMINES

[75] Inventors: Neal J. Grice; John F. Knifton, both of Austin, Tex.; Chau-Hwa Yang, Hopewell Junction, N.Y.

[73] Assignee: Texaco Inc., White Plains, N.Y.

[21] Appl. No.: 163,355

[22] Filed: Mar. 2, 1988

[51] Int. Cl.$^4$ .......................... B01J 21/06; B01J 27/18
[52] U.S. Cl. ....................................... 502/208
[58] Field of Search ........................................ 502/208

[56]   References Cited
   FOREIGN PATENT DOCUMENTS
   275620  7/1988  European Pat. Off. ............ 502/208
   55-157329 12/1980 Japan .................................... 502/208

Primary Examiner—W. J. Shine
Attorney, Agent, or Firm—Jack H. Park; Kenneth R. Priem; Carl G. Ries

[57]   ABSTRACT

This invention relates to a method for the preparation of predominantly linear polyethylenepolyamines by reacting ethylenediamine with monoethanolamine in the presence of a phosphorus/titania/zirconia catalyst.

The catalysts that are used in accordance with the present invention are composed of phosphorus, titania and zirconia. They are prepared by mixing solutions of a tetravalent compound of titanium with a tetravalent compound of zirconium, treating the solution to simultaneously heterogeneously coprecipitate titania and zirconia to form a heterogeneous titania/zirconia support, recovering the coprecipitate, treating it with a compound of phosphorus to bond from about 0.5 to 6 wt. % of phosphorus to the coprecipitate and then stabilizing the resultant catalyst by calcining it at about 200° to about 800° C.

25 Claims, 1 Drawing Sheet

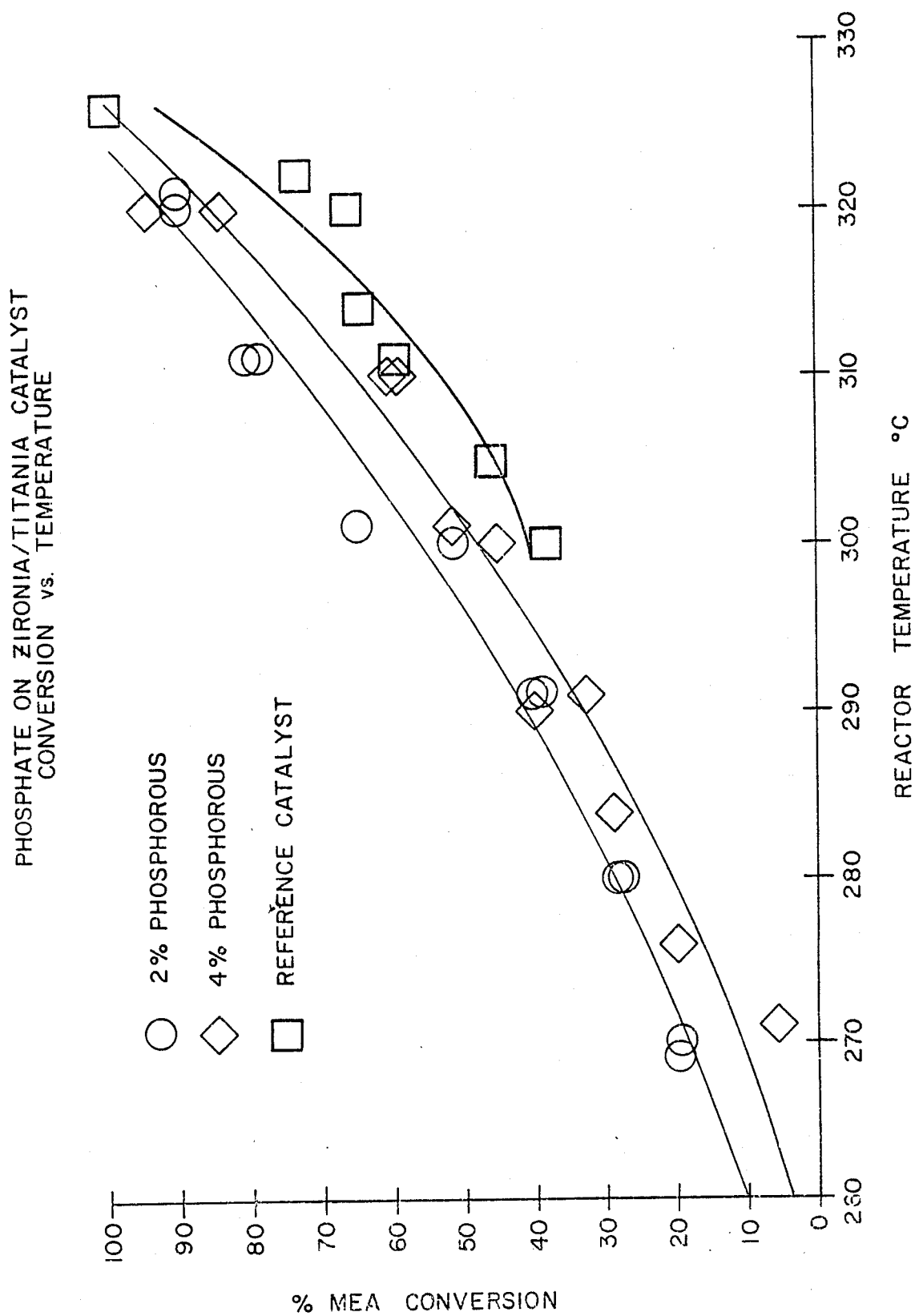

PHOSPHORUS/TITANIA/ZIRCONIA CATALYST FOR PREPARATION OF LINEAR POLYETHYLENEPOLYAMINES

BACKGROUND OF THE INVENTION

1. Technical Field of the Invention

This invention relates to a method for the preparation of predominantly linear polyethylenepolyamines by reacting ethylenediamine with monoethanolamine in the presence of a catalyst consisting essentially of phosphate supported on a heterogeneous titania/zirconia support.

The catalysts that are used in accordance with the present invention are composed of phosphorus, titania and zirconia. They are prepared by mixing solutions of a tetravalent compound of titanium with a tetravalent compound of zirconium, treating the solution to simultaneously coprecipitate titania and zirconia to form a heterogenous titania/zirconia support, recovering the coprecipitate, treating it with a phosphorus compound to bond from about 0.5 to 6 wt. % of phosphorus to the coprecipitate and then stabilizing the resultant catalyst by calcining it at about 200° to about 800° C.

2. Prior Art

Heretofore, polyethylenepolyamine compounds such as diethylenetriamine, triethylenetetramine and the higher homologs have been produced by the reaction of an alkyl halide such as ethylene dichloride with an amine such as ammonia or ethylenediamine at elevated temperatures and pressures. Normally, relatively high yields of predominantly noncyclic polyethylenepolyamine compounds are obtained from this process with varying yields of heterocyclic amines. The large amounts of energy required to produce the reactants as well as the difficult separation procedures required to recover the more valuable linear polyethylenepolyamines diminish the utility of the ethylene dichloride process. The hydrohalide salts of ammonia and the polyethylenepolyamine products must also undergo difficult and time consuming caustic neutralization to yield the free polyethylenepolyamines.

Investigators have found that more linear products can also be obtained in a catalytic conversion. Thus, Ford et al. U.S. Pat. No. 4,316,840 discloses the preparation of polyalkylenepolyamines from ethylenediamine utilizing a metal nitrate or sulfate as a catalyst. U.S. Pat. No. 4,314,083 discloses the reaction of ethylenediamine with monoethanolamine to prepare noncyclic polyalkylenepolyamines using, as a catalyst, a salt of a nitrogen or sulfur-containing compound.

Ford et al. U.S. Pat. No. 4,362,886 discloses a process for preparing predominantly non-cyclic polyalkylenepolyamine compounds from feedstocks such as ethylenediamine and ethanolamine using a compound of antimony, bismuth or arsenic as a catalyst. In Ford et al. U.S. Pat. No. 4,399,308, a Lewis acid halide is used to catalyze the reaction. In European patent application No. 0073520, Ford et al. disclose the use of a phosphorous-containing substance such as boron phosphate or a salt of a sulfur-containing substance such as beryllium sulfate, boron sulfate or ammonium sulfate as the catalyst.

Brennan et al. U.S. Pat. No. 4,036,881 discloses the use of phosphorous-containing catalysts to catalyze the reaction of ethylenediamine with monoethanolamine.

In Vanderpool U.S. Pat. No. 4,524,152, entitled "Catalytic Preparation of Linear Polyethylenepolyamines with Supported Catalysts", a process for the preparation of linear polyethylenepolyamines is disclosed wherein monoethanolamine is reacted with ethylenediamine in the presence of zirconium silicate to which phosphorous has been thermally bonded. Vanderpool U.S. Pat. No. 4,588,842 entitled "Catalytic Preparation of Polyethylenepolyamines" discloses the use of zirconia having phosphorous thermally bonded thereto as a catalyst for promoting the reaction of ethylenediamine with monoethanolamine to provide essentially linear polyethylenepolyamine reaction products.

In addition, Vanderpool U.S. Pat. No. 4,540,822 issued Sept. 10, 1985 discloses a process for making essentially linear polyethylenepolyamines by reacting monoethanolamine with ethylenediamine in the presence of a catalyst composed of a minor amount of phosphorus thermally, chemically bonded to a group IVb metal oxide support wherein the catalyst is periodically regenerated. In Vanderpool et al. U.S. Pat. No. 4,609,761 which issued Sept. 2, 1986, a catalyst for this reaction is disclosed wherein a trialkyl phosphate or a trialkyl phosphite is initially deposited on titania as a source of phosphorus, and in Renken U.S. Pat. No. 4,612,397 which issued Sept. 16, 1986, a diammonium hydrogen phosphate is used as a source for the phosphorus in preparing the catalyst.

French Pat. No. 1,317,359 dated Feb. 8, 1963, discloses the preparation of granulated zirconium phosphate and its use as an ion-exchange resin. Winkler et al. in a 1966 publication [Deutsche Akad. Wiss., Berlin, Germany, Z. Anorg. Allgen. Chem. 346 (1–2), 92–112 (1966)] disclose compounds of the general formula $HX^vP_2O_3$ wherein X represents arsenic, antimony and mixtures thereof. Also disclosed are compounds of the general formula $H_2X^{iv}P_2O_3$, wherein X represents silicon, germanium, tin, lead, titanium and zirconium. It is shown that the group IV phosphates have cation exchange properties.

SUMMARY OF THE INVENTION

This invention is directed to phosphorus-containing titanium/zirconia catalysts and to the preparation of essentially linear polyethylenepolyamines by reacting monoethanolamine with ethylenediamine in the presence of such phosphorus-containing catalysts. More particularly, this invention is directed to catalyst compositions consisting essentially of about 0.5 to 7 wt. % of phosphorus thermally, chemically bound to a heterogeneous coprecipitated mixture of titania and zirconia, such mixture containing about 40 to about 60 wt. % of titania and, correspondingly, about 60 to about 40 wt. % of zirconia and to the preparation of essentially linear polyethylenepolyamines by the reaction of monoethanolamine with ethylenediamine in the presence of such catalysts.

Still more particularly, this invention, in one aspect, relates to a method for preparing a catalyst composition by the controlled coprecipitation of titania and zirconia from an organic solvent solution of a tetravalent alkoxide, halide, nitrate, etc., of titanium and zirconium, to the recovery and drying of the coprecipitated mixture of titania and zirconia, to the phosphating treatment of the coprecipitate with an aqueous solution of a water soluble compound of phosphorus to cause from about 0.5 to 6 wt. % of phosphorus to bond to the coprecipitate and to the stabilization of the phosphated coprecipitate by calcination at a temperature of about 200° to about 800° C. to thereby provide a titania/zirconia catalyst support to which about 0.5 to 6 wt. % of phosphorus is thermally, chemically bound in the form of hydroxy-containing phosphate groups. In another aspect, this invention relates to catalyst compositions prepared in the described manner and in yet another aspect, this invention relates to a method of preparing essentially linear polyethylenepolyamines by reacting monoethanolamine with ethylenediamine in the presence of a phosphated titania/zirconia catalyst prepared by the described method under conversion conditions including a temperature of about 250° to about 400° C. and a pressure of about 500 to about 3000 psig.

DETAILED DESCRIPTION

Catalyst Compositions

The starting materials used to prepare the catalyst compositions of the present invention include a water soluble phosphorus compound containing hydroxyl groups and phosphorus-oxygen bonds, a tetravalent titanium compound and a tetravalent zirconium compound.

The tetravalent compounds of titanium and zirconium that are used as starting materials include tetravalent halides, nitrates, alkoxides, etc. The tetravalent aliphatic organo compounds of titanium and zirconium are preferred. Thus, for example, titanates and zirconates such as the $C_1$ to $C_4$ tetralkoxides of titanium and/or zirconium may be used, such as titanium and/or zirconium tetramethoxides, tetraethoxides, tetrapropoxides, tetrabutoxides, etc., or mixtures thereof, titanium and/or zirconium tetrachloride, tetrabromide, etc., titanium/zirconium nitrates, etc., may be used.

Preferably, and for ease of processing, the titanium compound and the zirconium compound will be analogues (e.g., titanium tetrabutoxide and zirconium tetrabutoxide).

Organic solvent solutions are prepared from the titanium compound and the zirconium compound, which are thereafter mixed or, alternatively, a single solution may be formulated from the titanium compound and the zirconium compound. The solution containing the titanium compound and the zirconium compound, in admixture, will suitably contain from about 40 to about 60 mole % of the titanium compound and, correspondingly, from about 60 to about 40 mole percent of the zirconium compound/

Many of the zirconium and titanium compounds, such as the titanates and the zirconates, are rapidly hydrolyzed to titania and zirconia in the presence of water and, therefore, the solvent that is used is preferably a polar organic solvent such as a $C_1$ to $C_4$ alkanol such as methanol, ethanol, propanol, isopropanol, a $C_1$ to $C_4$ monocarboxylic acid such as formic acid, acetic acid, propionic acid, butyric acid, etc., and the $C_1$ to $C_4$ alkyl esters thereof such as the methyl, ethyl, propyl or butyl formates, acetates, propionates, butyrates, etc., may be used.

The solution or solutions of the titanium and zirconium compounds need not be, but preferably, are essentially saturated solutions of the titanium and zirconium compound containing, on the basis of the combined weight of the titanium and zirconium compound, from about 0.1 to about 10 wt. % of the compounds preferably from about 0.5 to about 10 wt. % of the compounds.

The other starting material is a water or organically soluble phosphorus compound containing hydroxyl groups and phosphorus-oxygen bonds. Preferably an aqueous solution containing about 10 to about 85 wt. % of an acid of phosphorus, such as phosphoric acid, phosphorous acid, polyphosphoric acid, etc., is used. However, other liquid phosphorus compounds may be used, including, for example, alkyl phosphates and alkyl phosphites such as trimethyl phosphate, triethyl phosphate, trimethyl phosphite, triethyl phosphite, etc. Also, a diaminohydrogen phosphate such as diammonium hydrogen phosphate, $(NH_4)_2HPO_4$, dimethyldiamino hydrogen phosphate, $(CH_3)_2NH\ PO_4$, diethylaminohydrogen phosphate $(CH_3CH_2)_2NH\ PO_4$, etc. may be used.

As a matter of convenience, the normal practice is to use only one chemical as a phosphorus source (e.g., aqueous phosphoric acid). However, mixtures of two or more such reagents may be used, if desired.

Catalyst Preparation

As indicated above, the first step in the catalyst preparation process of the present invention is the preparation of a polar organic solvent solution of tetravalent compounds of titanium and zirconium, the solution containing about 0.01 to about 50 wt. % of the mixture of the tetravalent titanium compound with the tetravalent zirconium compound, on the basis of the combined weight of the tetravalent compounds. Also, the compounds should be proportioned so that the tetravalent titanium compound constitutes about 40 to 60 wt. % of the mixture of tetravalent titanium and zirconium compounds and so that the zirconium compound correspondingly constitutes about 60 to about 40 wt. % of the mixture.

Next, the solution is treated so as to cause the formation of a mixed heterogeneous precipitate of titania and zirconia. This can be accomplished in any suitable manner known to those skilled in the art, such as by conversion of the tetravalent titanium and zirconium compounds into unsoluble titania and zirconia by treating the solution with an appropriate hydrolysing agent such as water, etc. Preferably, the solution is treated with a precipitating agent such as water, ammonium hydroxide, etc., in the same solvent used in the preparation of the primary solution. Thus, for example, if the primary solvent is an alkanol such as isopropanol, the precipitating solution would comprise about a 0.1 to 50 wt. % solution of water in the alkanol, made basic to a pH of about eight or more with a suitable base such as ammonia.

The primary solution and the precipitating solution are then mixed and agitated for about 0.1 to about 6 hours to insure complete precipitation of the titania and the zirconia. At the end of the holding (digestion period), the precipitated heterogeneous mixture of titania with zirconia are recovered by any suitable means such as decantation, evaporation, filtration, centrifugation, etc., thoroughly wash with water, and dried.

The thus-prepared heterogeneous titania/zirconia support may be treated with a phorphorus-containing compound in powdered form, particularly when the catalyst is to be used in a batch-reaction sequence. However, the catalyst will normally be used in a continuous process and is therefore preferably used in the form of a fixed bed of catalyst pellets through which the reactants flow. When the catalyst is to be used in pelleted form, the heterogeneous mixture of precipitated titania and zirconia may be treated with a phosphorus compound prior to or subsequent to the pelleting operation. Preferably, the precipitate will be pelleted and then treated with the phosphorus compound. Pelleting can be accomplished in any suitable manner known to those skilled in the art. For example, the precipitate may be mixed with from about 1 to 5 wt. % of binders and lubricants such as graphite, sterotex, etc., and then compacted in a pelleting machine at a pressure of about 10 psig or more. The pellets will suitably have a surface area of about 10 to about 1,000M$^2$/gram, preferably 100 to 1,000M$^2$ per gram.

It is customary to use cylindrically-shaped catalyst pellets having a diameter essentially equal to the length thereof, such as diameters and lengths ranging from about 1/32" to about ⅜". It will be understood that the shape and dimensions of the pellets are not critical to the present invention and that pellets of any suitable shape and dimensions may be used as desired, by one wishing to practice the process of the present invention.

Titania is characterized as a solid having the formula TiO$_2$ and zirconia is characterized as a solid having the formula ZrO$_2$. The compounds exist as crystalline solids such as anatase or rutile (titania) or baldsleyite (zirconia) containing, for example, recurring (TiO)TiO$_3$ units and dispersed HO(TiO$_3$) units on the surface of the crystals. The coprecipitates of the present invention differ from titania and zirconia in that the titanium and zirconium atoms are randomly distributed, thereby altering the structure of the crystals. It is believed that hydroxyl groups are present on the surface to titania/zirconia precipitate and that the hydroxyl groups will react with organic or water-soluble phosphorus compounds containing phosphorus-oxygen bonds, at least to the extent that reaction products containing from about 0.5 to about 6 wt. % of phosphorus are formed. This is surprising, because titania and zirconia are essentially insoluble in organic solvents and water. However, solutions of phosphorus compounds containing phosphorus-oxygen bonds, as described above, have the capacity to wet the surface of the titania and zirconia at least to an extent sufficient to permit a limited reaction of the titania and zirconia with the phosphorus compound.

It is believed that the reaction may proceed as follows:

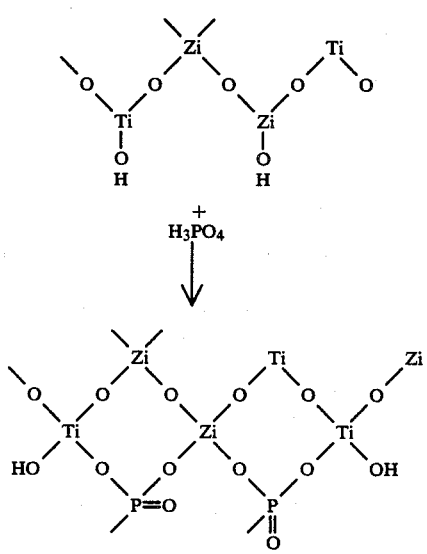

In accordance with the present invention, the coprecipitate in pelleted or powdered form is immersed in the organic or aqueous solution of the phosphorus compound by an appropriate procedure (described hereafter) at an appropriate temperature, such as ambient temperature (e.g., 20°–30° C.) or a higher temperature, such as a temperature at or above the boiling point of the solution of the phosphorus compound (e.g., 100° to 150° C.). Temperatures below ambient temperature may be used, if desired, but no particular advantage is obtained by cooling the solution of the phosphorus compound for the impregnation step. However, temperatures between ambient temperature and the boiling point of the aqueous solution of the phosphorus compound can be used, if desired. Thus, the appropriate impregnation temperature range that will normally be used is from about 20° to about 150° C. Suitable organic solvents for the phosphorus compound include volatile ketones such as acetone, with boiling points of less than about 150° C.

Immersion time is not critical, but the pellets should be immersed long enough for the solution to impregnate at least the outer porous surface (and more preferably, the entire porous structure) of the coprecipitate. Normally, then, a minimum immersion time at ambient temperature or at temperatures between ambient temperature and the boiling point of the aqueous solution will be about 1 minute and, more preferably, about 0.1 to about 5 hours.

After immersion, the coprecipitate is removed from the solution of the phosphorus compound and allowed to drain.

It has ben discovered in accordance with the present invention that immersion of the coprecipitate in the aqueous or organic solution will cause a portion of the phosphorus compound to adhere to the pellets, such that the impregnated pellets will now contain from about 0.5 to about 6 wt. % of phosphorus.

When the pellets are immersed and drained at a temperature below about 100° C., the phosphorus is not completely "fixed" to the coprecipitate and can be partially removed (e.g., by washing the pellets with water). Therefore, a heating step is necessary to permanently chemically bond the phosphorus to the coprecipitate and the heating step is preferably a calcining step (hereafter described in greater detail) because calcination is necessary in order to stabilize the pellets. However, if desired, an intermediate heating step conducted at about 100° to about 200° C. for about 0.5 to about 5 hours may be conducted in order to thermally, chemically bond the phosphorus to the coprecipitate. Calcination will occur when the impregnated pellets are heated at or above about 200° C.

Another procedure to be used is to heat the solution of the phosphorus compound to a temperature of about 100° to about 150° C. and to then add the coprecipitate (preferably in pelleted form) in an amount about equal to the volume of the heated liquid. This treatment should be continued from about 0.5 to about 5 hours, depending upon the phosphorus compound used. At the end of that time, the resulting mixture of pellets and liquid is cooled, decanted to remove excess liquid followed by washing with an amount of water adequate to substantially completely remove unadsorbed liquid.

It has been further discovered in accordance with the present invention that the immersion and chemical bonding steps, just described, result in a composition consisting essentially of a coprecipitate of titania and zirconia having from about 0.5 to about 6 wt. % of phosphorus thermally, chemically bonded to at least the surface thereof.

It will be understood that the phosphorus that is present on a thus-treated coprecipitate is not present as elemental phosphorus, but rather as phosphorus that is chemically bound, normally as an oxide, to the group IVb metal oxide support. This is demonstrated by the fact that repeated washing will not remove all of the phosphorus. The exact nature of the bonding is not completely understood.

However, the catalyst compositions of the present invention can be characterized as compositions composed of a pelleted or unpelleted coprecipitate of titania and zirconia having from about 0.5 to about 6 wt. % of phosphorus chemically bonded to the surface thereof through titania oxygen or zirconia oxygen bonds in the form of hydroxy-containing phosphate groups. If all of the P—O+ valence bonds are chemically interconnected with the group IVb transition metal oxide, the resultant composition will be essentially inert insofar as activity for catalyzing the reaction of monoethanolamine with ethylenediamine is concerned.

The amount of phosphorus that is bonded to the support is a function of heating and other conditions used in the treating step and is also a function of the chemical identity of the phosphorus compound that is used as a source of phosphorus. Under the treating conditions exemplified above, at least about 0.5 wt. % of phosphorus is caused to bond or otherwise permanently adhere to the coprecipitate. There is an upper limit to the amount of phosphorus that bonds or otherwise permanently adheres to the coprecipitate. This upper limit is, as indicated, a function of both the treating conditions and the chemical used as a source of the phosphorus. Normally, not more than about 6 wt. % of phosphorus can be caused to bond to the pellets.

The pelleted catalyst compositions of the present invention should be calcined. They can be calcined prior to use or calcined in situ when used as catalysts at temperatures in excess of about 200° C. When the catalysts are to be calcined prior to use, calcination is suitably conducted for 2 to 24 hours at a temperature of 200° C. but below the temperature at which thermal destruction of the phosphorus bonding occurs. This can be determined experimentally for a particular catalyst. Temperatures above 900° C. should be avoided. A suitable calcining temperature range is normally 200° to 800° C. and, more preferably, 300° to 600° C.

In any event, in-situ calcining will occur when the pelleted compositions are used to catalyze the reaction of monoethanolamine with ethylenediamine at 250° to 450° C.

Preparation of Polyethylenepolyamines

The catalyst compositions of the present invention catalyze the reaction of ethylenediamine and monoethanolamine at a temperature of from about 250° C. to about 400° C., preferably from about 300° C. to about 350° C. and a pressure of from about 500 to about 3,000 psi. The ratio of ethylenediamine to monoethanolamine may range from about 1:2 to about 5:1. Higher temperatures or higher pressures may be used, but there is no particular advantage in using higher temperatures and/or pressures.

The pelleted catalyst compositions of the present invention are normally employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc., in order to obtain a desired rate of reaction and, hence, a desired percentage of conversion of the reactants. Thus, in a continuous process, it is not necessary to drive the reaction to completion because unreacted feedstock components can be recycled to the reactor.

When cylindrical pellets of catalyst of the type described above are used, the weighted hourly space velocity may be varied within wide limits (e.g., 0.1 to 5 w/hr/w) in order to obtain a desired rate of conversion, as explained above. Normally, space velocities of about 0.5 to 2 w/hr/w will be employed.

The catalysts of the present invention may also be employed in powdered form, in which case the reaction can be conducted on a batch basis in an autoclave. When the reaction is conducted in an autoclave, the reaction conditions to be employed include a temperature within the range of about 250° to about 400° C., at autogeneous pressure, a molar ratio of ethylenediamine to monoethanolamine of about 0.5 to about 5.0 and a reaction time of about 0.5 to about 6 hours. Higher or lower pressures may be used, if desired, but there is no particular advantage in doing so.

There are many compounds which can be formed from the reaction of ethylenediamine and monoethanolamine besides the preferred linear polyethylenepolyamines such as diethylenetriamine, triethylenetetramine, tetraethylenepentamine and pentaethylenehexamine. Less desirable cyclics and other compounds, such as piperazine, N-(2-aminoethyl)ethanolamine and N-(2-aminoethyl)piperazine, are also formed. The more desired linear polyethylenepolyamines can be easily recovered from the reaction product mixture by conventional methods such as distillation. Such distillation recovery methods are well known in the art. An outstanding advantage of the claimed invention is that the lower molecular weight polyethlenepolyamines recovered from the reaction mixture can be further reacted with monoethanolamine to produce a larger percentage of the higher molecular weight linear polyethylenepolyamines.

The following examples will further illustrate the preparation of predominantly linear polyethylenepolyamines from ethylenediamine and monoethanolamine by the use of the catalyst compositions of the present invention. They are given by way of illustration and not as limitations on the scope of the invention. Thus, it will be understood that reactants, proportions of reactants, and time, temperature and pressure of the reaction steps may be varied with much the same results achieved.

For purposes of convenience and brevity, the reactant compounds employed and the products obtained have been abbreviated in the following examples and table. The abbreviations employed for these various compounds are:

EDA—ethylenediamine
MEA—monoethanolamine
PIP—piperazine
DETA—diethylenetriamine
TETA—triethylenetetramine
TEPA—tetraethylenepentamine
AEEA—N-(2-aminoethyl)ethanolamine
AEP—N-(2-aminoethyl)piperazine
HEP—N-(hydroxyethyl)piperazine
DIAEP—diaminoethylpiperazine
DEEDA—diethylene ethylenediamine AETETA—aminoethyltriethylene tetramine

EXAMPLES

The present invention will be further illustrated by the following working examples and the accompanying drawing where:

BRIEF DESCRIPTION OF THE DRAWING

The FIGURE is a graph illustrating the conversion of monoethanolamine obtained with a catalyst of the present invention, in comparison with a reference catalyst, as a function of the percent of the reaction temperature.

I. Preparation

A solution of 1 part by weight of titanium isopropoxide $Ti(OiPr)_4$ [iPr is isopropyl] and 1 pbw. zirconium n-propoxide $Zr(OnPr)_4$ in 2 pbw. isopropanol was hydrolyzed by adding an equal amount of basic aqueous isopropanol and digesting overnight. The basic aqueous isopropanol was prepared by combining equal weights of isopropanol and water brought to pH=10.4 with aqueous ammonia. The digested catalyst was collected by filtration and washed 5 to 6 times with water then dried at 110° C. in air. It was then calcined at 500° C. in air for 4 hours and tabletted with 1-2% sterotex binder to ⅛"×⅛" dimensions. The surface area of this support was determined to be $340M^2$/gram.

II. Catalyst Preparation

The support (51.5 g.) was dried under <0.1 mm vacuum then a solution of 7.1 g. 85% reagent phosphoric acid in 50 cc. of reagent acetone was added to it with agitation at 15 mm. vacuum. Periodic agitation under vacuum at ambient temperature was provided using a rotor evaporator until all the liquid had disappeared and the solid was free flowing. The catalyst was then warmed to 60° C. under these conditions for one hour. The catalyst was transferred to a glass tubular furnace and heated to 150° C. for 1 hour under $N_2$ flow then calcined at 350° C. under $N_2$ flow for two hours. The formulated catalyst (6030-64) volume was 60 cc and contained 2 wt. % phosphorus.

III. Application of Catalyst-A

The above catalyst was placed in a stainless steel tube in an aluminum heating block (50 cc of catalyst). Through the tube was passed a mixture of ethylenediamine (EDA) (2 pbw) and monoethanolamine (MEA) (1 pbw) at a rate of 100 cc per hour. The apparatus was held at a series of temperatures 3 to 4 hours to allow equilibration and samples were taken for analysis by GLC. The area % analysis, along with the calculated % MEA conversion, % EDA conversion, DETA/Piperazine ratio, and percent non-cyclic products in the TETA range as well as the relative selectivities among the observed products is presented for each of the samples in Tables I-A through I-C.

IV. Catalyst Preparation-B

Following the procedure of catalyst preparation-A, a sample of the zirconia-titania support (51 g) was treated with a solution of 14.2 g of 85% reagent phosphoric acid in acetone. The resulting catalyst (6147-7) contained 4 wt. % phosphorus.

V. Application of Catalyst-B

Following the procedure of Example III, the catalyst of preparation-B (50 cc) was evaluated for ethylenediamine/monoethanolamine reaction over a range of temperatures.

The results, particularly the observed products and selectivities are presented for each of the samples in Tables II-A through II-C.

VI. Use of Reference Catalyst to Prepare Ethyleneamines

In order to provide a comparison of the improvement in catalyst activity that is obtainable with the catalysts of the present invention, a reference catalyst was also used to catalyze the reaction of ethylene diamine with monoethanolamine in the manner and in the equipment described above. The reference catalyst was a titania-supported phosphorus catalyst prepared by immersing titania pellets in concentrated phosphoric acid, after which the immersed titania was drained of excess liquid and then calcined. The reference catalyst had been used for extensive pilot plant studies of the process of reacting ethylene diamine with monoethanolamine and had been found to be the most consistently active catalyst of all of the catalysts that were tested.

The results of this series of tests are given in Table III.

TABLE I-A

Ethyleneamines Continuous Reactor Products
(2% P) Phosphoric Acid on High Surface Area Zirconia/Titania
Catalyst 6030-64

| 1 Sample 6030-65 | 2 Temp. °C. | 3 Area % EDA | 4 Area % MEA | 5 % MEA Conv. | 6 Area % PIP | 7 % Selec. to PIP | 8 Area % BAEE | 9 % Selec. to BAEE | 10 % Conv. of EDA | 11 Area % DETA | 12 % Selec. to DETA |
|---|---|---|---|---|---|---|---|---|---|---|---|
| Feed | | 66.81 | 33.18 | | | | | | | | |
| 1 | 270 | 64.59 | 26.76 | 19.35 | 0.06 | 0.72 | 0.00 | 0.00 | 3.32 | 8.37 | 97.54 |
| 2 | 269 | 66.00 | 26.63 | 19.73 | 0.01 | 0.19 | 0.00 | 0.00 | 1.21 | 7.18 | 98.42 |
| 3 | 280 | 63.51 | 23.74 | 28.44 | 0.15 | 1.25 | 0.00 | 0.00 | 4.94 | 11.51 | 91.68 |
| 4 | 280 | 63.03 | 24.05 | 27.51 | 0.18 | 1.48 | 0.00 | 0.00 | 5.66 | 11.64 | 91.52 |
| 5 | 291 | 60.86 | 19.79 | 40.34 | 0.44 | 2.42 | 0.00 | 0.00 | 8.91 | 14.97 | 81.42 |
| 6 | 291 | 60.39 | 20.30 | 38.82 | 0.34 | 1.86 | 0.00 | 0.00 | 9.61 | 15.40 | 83.32 |
| 7 | 300 | 57.79 | 16.19 | 51.20 | 0.66 | 2.72 | 0.03 | 0.14 | 13.49 | 18.82 | 77.21 |
| 8 | 301 | 60.17 | 11.68 | 64.79 | 0.69 | 2.68 | 0.00 | 0.00 | 9.93 | 19.66 | 76.02 |
| 9 | 311 | 54.50 | 6.43 | 80.59 | 1.27 | 3.75 | 0.09 | 0.26 | 18.42 | 22.90 | 67.25 |
| 10 | 311 | 54.81 | 6.96 | 79.01 | 1.30 | 7.94 | 0.09 | 0.29 | 17.96 | 23.05 | 69.98 |
| 11 | 320 | 49.33 | 3.28 | 90.11 | 2.12 | 5.42 | 0.12 | 0.31 | 26.16 | 23.51 | 60.15 |
| 12 | 321 | 49.97 | 3.34 | 89.91 | 2.11 | 5.45 | 0.10 | 0.26 | 25.20 | 23.67 | 61.01 |

TABLE I-B

| 1 Sample 6030-65 | 13 Area % AEEA | 14 % Selec. to AEEA | 15 Ratio: Obsv. DETA/ Obsv. PIP | 16 Area % of AEP | 17 % Selec. of AEP | 18 Area % NTEA | 19 % Selec. to NTEA | 20 % of NC | 21 Area % of TETA | 22 % Selec. of TETA |
| --- | --- | --- | --- | --- | --- | --- | --- | --- | --- | --- |
| 1 | 0.12 | 1.42 | 135.14 | 0.02 | 0.31 | 0.00 | 0.00 | | 0.00 | 0.00 |
| 2 | 0.07 | 1.08 | 513.35 | 0.02 | 0.30 | 0.00 | 0.00 | | 0.00 | 0.00 |
| 3 | 0.23 | 1.86 | 72.84 | 0.08 | 0.65 | 0.06 | 0.49 | 100.00 | 0.50 | 4.04 |
| 4 | 0.21 | 1.69 | 61.62 | 0.08 | 0.66 | 0.06 | 0.52 | 100.00 | 0.52 | 4.10 |
| 5 | 0.25 | 1.37 | 33.57 | 0.22 | 1.23 | 0.21 | 1.16 | 99.31 | 2.24 | 12.20 |
| 6 | 0.26 | 1.42 | 44.79 | 0.20 | 1.11 | 0.17 | 0.96 | 98.45 | 2.05 | 11.11 |
| 7 | 0.20 | 0.82 | 28.35 | 0.47 | 1.95 | 0.30 | 1.26 | 99.60 | 3.72 | 15.27 |
| 8 | 0.20 | 0.80 | 28.29 | 0.47 | 1.85 | 0.40 | 1.56 | 99.13 | 4.05 | 15.65 |
| 9 | 0.16 | 0.47 | 17.91 | 1.06 | 3.13 | 0.50 | 1.47 | 95.34 | 6.46 | 18.99 |
| 10 | 0.19 | 0.62 | 17.72 | 0.04 | 0.12 | 0.48 | 1.52 | 97.53 | 6.50 | 19.73 |
| 11 | 0.00 | 0.00 | 11.08 | 1.85 | 4.75 | 0.51 | 1.32 | 91.68 | 8.13 | 20.79 |
| 12 | 0.00 | 0.00 | 11.18 | 1.81 | 4.68 | 0.49 | 1.27 | 92.14 | 7.90 | 20.37 |

TABLE I-C

| 1 Sample 6030-65 | 23 Area % of DIAEP | 24 % Selec. of DIAEP | 25 Area % of PEEDA | 26 % Selec. of PEEDA | 27 Area % of AETETA | 28 % Selec. to AETETA | 29 Area % of TEPA | 30 % Selec. of ETPA | 31 Total Product |
| --- | --- | --- | --- | --- | --- | --- | --- | --- | --- |
| 1 | 0.00 | 0.00 | 0.00 | 0.00 | 0.00 | 0.00 | 0.00 | 0.00 | 8.59 |
| 2 | 0.00 | 0.00 | 0.00 | 0.00 | 0.00 | 0.00 | 0.00 | 0.00 | 7.30 |
| 3 | 0.00 | 0.00 | 0.00 | 0.00 | 0.00 | 0.00 | 0.00 | 0.00 | 12.55 |
| 4 | 0.00 | 0.00 | 0.00 | 0.00 | 0.00 | 0.00 | 0.00 | 0.00 | 12.72 |
| 5 | 0.00 | 0.00 | 0.01 | 0.09 | 0.01 | 0.08 | 0.00 | 0.00 | 18.39 |
| 6 | 0.01 | 0.10 | 0.01 | 0.08 | 0.00 | 0.00 | 0.00 | 0.00 | 18.49 |
| 7 | 0.01 | 0.06 | 0.00 | 0.00 | 0.13 | 0.53 | 0.00 | 0.00 | 24.38 |
| 8 | 0.03 | 0.15 | 0.00 | 0.00 | 0.15 | 0.59 | 0.17 | 0.66 | 25.86 |
| 9 | 0.16 | 0.47 | 0.17 | 0.51 | 0.32 | 0.95 | 0.91 | 2.69 | 34.05 |
| 10 | 0.17 | 0.55 | 0.00 | 0.00 | 0.96 | 2.91 | 0.12 | 0.37 | 32.94 |
| 11 | 0.39 | 1.00 | 0.39 | 1.00 | 1.74 | 4.45 | 0.29 | 0.76 | 39.08 |
| 12 | 0.33 | 0.87 | 0.37 | 0.97 | 0.40 | 1.03 | 1.57 | 4.04 | 38.08 |

TABLE II-A

Ethyleneamines Continuous Reactor Products
(4% P) Phosphoric Acid on High Surface Area Zirconia/Titania
Catalyst 6147-7

| 1 Sample 6147-8 | 2 Temp. °C. | 3 Area % EDA | 4 Area % MEA | 5 % MEA Conv. | 6 Area % PIP | 7 % Selec. of PIP | 8 Area % BAEE | 9 % Selec. to BAEE | 10 % Conv. of EDA | 11 Area % DETA | 12 % Selec. to DETA |
| --- | --- | --- | --- | --- | --- | --- | --- | --- | --- | --- | --- |
| Feed | | 66.81 | 33.18 | | | | | | | | |
| 1 | 271 | 62.31 | 31.30 | 5.67 | 0.00 | 0.00 | 0.00 | 0.00 | 6.73 | 6.38 | 76.13 |
| 2 | 276 | 62.12 | 26.61 | 19.81 | 0.09 | 0.88 | 0.00 | 0.00 | 7.01 | 10.78 | 96.88 |
| 3 | 284 | 61.89 | 23.57 | 28.94 | 0.24 | 1.75 | 0.00 | 0.00 | 7.36 | 13.05 | 91.89 |
| 4 | 290 | 59.23 | 19.91 | 39.97 | 0.36 | 2.03 | 0.00 | 0.00 | 11.34 | 15.74 | 87.26 |
| 5 | 291 | 59.79 | 22.37 | 32.58 | 0.29 | 1.68 | 0.00 | 0.00 | 10.51 | 15.65 | 89.51 |
| 6 | 301 | 59.83 | 16.13 | 51.38 | 0.65 | 2.86 | 0.03 | 0.14 | 10.45 | 18.02 | 78.72 |
| 7 | 300 | 57.86 | 18.23 | 45.05 | 0.61 | 2.65 | 0.00 | 0.00 | 13.39 | 18.23 | 79.37 |
| 8 | 310 | 55.17 | 13.14 | 60.38 | 0.97 | 3.31 | 0.03 | 0.11 | 17.41 | 21.09 | 71.84 |
| 9 | 310 | 54.97 | 13.64 | 58.87 | 0.99 | 3.38 | 0.03 | 0.11 | 17.72 | 21.01 | 71.71 |
| 10 | 320 | 49.05 | 5.29 | 84.03 | 1.87 | 4.96 | 0.17 | 0.46 | 26.58 | 23.37 | 61.88 |
| 11 | 320 | 51.99 | 1.96 | 94.09 | 1.83 | 4.71 | 0.07 | 0.19 | 22.18 | 24.82 | 63.74 |

TABLE II-B

| 1 Sample 6147-8 | 13 Area % AEEA | 14 % Selec. to AEEA | 15 Ratio: Obsv. DETA/ Obsv. PIP | 16 Area % of AEP | 17 % Selec. of AEP | 18 Area % NTEA | 19 % Selec. to NTEA | 20 % of NC | 21 Area % of TETA | 22 % Selec. of TETA |
| --- | --- | --- | --- | --- | --- | --- | --- | --- | --- | --- |
| 1 | 0.00 | 0.00 | | 2.00 | 23.86 | 0.00 | 0.00 | | 0.00 | 0.00 |
| 2 | 0.17 | 1.59 | 110.04 | 0.00 | 0.00 | 0.00 | 0.00 | 100.00 | 0.07 | 0.64 |
| 3 | 0.35 | 2.50 | 52.43 | 0.10 | 0.73 | 0.08 | 0.57 | 100.00 | 0.36 | 2.54 |
| 4 | 0.33 | 1.83 | 42.77 | 0.18 | 1.03 | 0.14 | 0.79 | 98.23 | 1.24 | 6.89 |
| 5 | 0.34 | 1.98 | 53.07 | 0.18 | 1.05 | 0.12 | 0.70 | 97.61 | 0.86 | 4.91 |
| 6 | 0.29 | 1.30 | 27.51 | 0.45 | 1.96 | 0.28 | 1.24 | 97.20 | 2.98 | 13.03 |
| 7 | 0.40 | 1.77 | 29.88 | 0.39 | 1.70 | 0.31 | 1.38 | 97.47 | 2.81 | 12.25 |
| 8 | 0.34 | 1.17 | 21.68 | 0.75 | 2.58 | 0.40 | 1.38 | 95.91 | 4.80 | 16.36 |
| 9 | 0.37 | 1.27 | 21.20 | 0.77 | 2.63 | 0.41 | 1.41 | 95.38 | 4.66 | 15.93 |
| 10 | 0.20 | 0.53 | 12.46 | 1.71 | 4.54 | 0.52 | 1.39 | 90.90 | 7.01 | 18.57 |
| 11 | 0.00 | 0.00 | 13.52 | 1.87 | 4.80 | 0.51 | 1.32 | 91.09 | 7.18 | 18.43 |

TABLE II-C

| Sample 6147-8 | Area % of DIAEP | % Selec. of DIAEP | Area % of PEEDA | % Selec. of PEEDA | Area % of AETETA | % Selec. to AETETA | Area % of TEPA | % Selec. of TEPA | Total Product |
|---|---|---|---|---|---|---|---|---|---|
| 1 | 0.00 | 0.00 | 0.00 | 0.00 | 0.00 | 0.00 | 0.00 | 0.00 | 8.38 |
| 2 | 0.00 | 0.00 | 0.00 | 0.00 | 0.00 | 0.00 | 0.00 | 0.00 | 11.13 |
| 3 | 0.00 | 0.00 | 0.00 | 0.00 | 0.00 | 0.00 | 0.00 | 0.00 | 14.20 |
| 4 | 0.02 | 0.13 | 0.00 | 0.00 | 0.00 | 0.00 | 0.00 | 0.00 | 18.04 |
| 5 | 0.02 | 0.13 | 0.00 | 0.00 | 0.00 | 0.00 | 0.00 | 0.00 | 17.49 |
| 6 | 0.05 | 0.22 | 0.04 | 0.18 | 0.00 | 0.00 | 0.07 | 0.31 | 22.89 |
| 7 | 0.04 | 0.20 | 0.03 | 0.15 | 0.11 | 0.50 | 0.00 | 0.00 | 22.96 |
| 8 | 0.10 | 0.36 | 0.11 | 0.38 | 0.28 | 0.95 | 0.44 | 1.51 | 29.36 |
| 9 | 0.12 | 0.41 | 0.12 | 0.41 | 0.31 | 1.07 | 0.47 | 1.61 | 29.29 |
| 10 | 0.36 | 0.96 | 0.38 | 1.02 | 0.48 | 1.28 | 1.64 | 4.35 | 37.77 |
| 11 | 0.35 | 0.89 | 0.40 | 1.03 | 0.46 | 1.20 | 1.41 | 3.64 | 38.94 |

TABLE III

Ethyleneamines Continuous Reactor Products
Reference Catalyst
Catalyst 5714-78

| Sample 5714-78 | Temp °C. | % MEA Conv. |
|---|---|---|
| 1 | 300 | 38.3 |
| 2 | 305 | 45.9 |
| 3 | 311 | 54.4 |
| 4 | 314 | 64.3 |
| 5 | 320 | 65.9 |
| 6 | 322 | 73.2 |
| 7 | 326 | 99.9 |

Turning now to the drawings, in the FIGURE the data from Tables I-A, I-B and I-C and Tables II-A, II-B and II-C has been plotted to show the conversion of monoethanolamine (MEA) obtained with the catalyst of the present invention, as compared with the reference catalyst, it will be noted that an almost constant 10% increase in conversion of MEA was obtained with the catalyst of the present invention (Examples II, 630–64). This result was surprising and unexpected, because the reference catalyst was the most effective catalyst known to the inventors prior to their discovery of the catalyst compositions of the present invention.

The foregoing examples have been given by way of illustration and not as limitations on the scope of this invention, as defined by the appended claims.

We claim:

1. A method for preparing a catalytically active composition consisting essentially of a pelleted heterogeneous coprecipitate of titania and zirconia having about 0.5 to about 6 wt. % of phosphorus thermally chemically bonded thereto in the form of hydroxy-containing phosphate groups, said method comprising the steps of:

preparing a polar organic solvent solution of a tetravalent aliphatic organic compound of titanium and a tetravalent aliphatic organic compound of zirconium, said polar organic solvent solution containing from about 0.1 to about 10 wt. % of said tetravalent compounds of titanium and zirconium, the weight of the tetravalent titanium compound comprising about 40 to about 60 wt. % of the combined weight of both the tetravalent titanium compound and the tetravalent zirconium compound and, correspondingly, the weight of the tetravalent zirconium compound comprising about 60 to about 40 wt. % of the said combined weight, adding an amount of a hydrolysing agent to said solution sufficient to hydrolyse said titanium compound and said zirconium compound to titania and zirconia, respectively, and to coprecipitate a heterogeneous mixture of titania and zirconia, recovering and washing said coprecipitated mixture of titania and zirconia, impregnating said coprecipitate with a solution of a phosphorus compound containing phosphorus-oxygen bonds at a temperature of about 20° to about 150° C., draining and drying said impregnated coprecipitate and then stabilizing said coprecipitate by calcination at a temperature within the range of about 200° to about 800° C. sufficient to thermally chemically bond about 0.5 to 6 wt. % of phosphorus to said pellets in the form of hydroxy-containing phosphate groups.

2. A method as in claim 1 wherein the tetravalent titanium compound is titanium tetraisopropoxide and the tetravalent zirconium compound is zirconium tetra-n-propoxide.

3. A method as in claim 2 wherein the hydrolyzing agent is an aqueous solution of isopropanol.

4. A method as in claim 3 wherein the aqueous solution of isopropanol is an aqueous ammoniacal solution of isopropanol.

5. A method as in claim 4 wherein the phosphorus compound is phosphoric acid.

6. A method for preparing a catalytically active composition consisting essentially of a pelleted coprecipitated heterogeneous mixture of titania and zirconia having about 0.5 to about 6 wt. % of phosphorus thermally chemically bonded to the surface thereof in the form of hydroxy-containing phosphate groups, said method consisting essentially of the steps of:

preparing a polar organic solvent solution of a tetravalent aliphatic organic compound of titanium and a tetravalent aliphatic organic compound of zirconium, said polar organic solvent solution containing from about 0.5 to about 10 wt. % of said tetravalent compounds of titanium and zirconium, the weight of the tetravalent titanium compound comprising about 40 to about 60 wt. % of the combined weight of both the tetravalent titanium compound and the tetravalent zirconium compound and, correspondingly, the weight of the tetravalent zirconium compound comprising about 60 to about 40 wt. % of said combined weight, adding an amount of a hydrolysing agent to said solution sufficient to hydrolyse said titanium compound and said zirconium compound to titania and zirconia, respectively, and to selectively coprecipitate a heterogeneous mixture of titania and zirconia, recovering, washing and pelleting said precipitated mixture of titania and zirconia, impregnating said pellets with an acetone solution of a phosphorus acid at a temperature of about 20° to about 150° C. for a period of time within the range of about 0.1 to 5 hours sufficient to thermally chemically bond said 0.5 to 6 wt. % of phosphorus to said pellets, water washing and drying said thus treated pellets to remove unabsorbed liquid and thereafter recovering and drying the thus-treated pellets.

7. A method as in claim 6, wherein the pellets are stabilized by a calcining step conducted at a temperature within a range from about 200° to about 800° C.

8. A method as in claim 7 wherein the tetravalent titanium compound is titanium tetraisopropoxide and the tetravalent zirconium compound is zirconium tetra-n-propoxide.

9. A method as in claim 8 wherein the hydrolyzing agent is an aqueous solution of isopropanol.

10. A method as in claim 9 wherein the aqueous solution of isopropanol is an aqueous ammoniacal solution of isopropanol.

11. A method as in claim 10 wherein the phosphorus compound is phosphoric acid.

12. As a new composition of matter, a catalytically active composition consisting essentially of a pelleted coprecipitated heterogeneous mixture of titania and zirconia having about 0.5 to about 6 wt. % of phosphorus thermally chemically bonded thereto in the form of hydroxy-containing phosphate groups, said composition having been prepared by a method comprising the steps of:

preparing a polar organic solvent solution of a tetravalent aliphatic organic compound of titanium and a tetravalent aliphatic organic compound of zirconium, said polar organic solvent solution containing from about 0.5 to about 10 wt. % of said tetravalent compounds of titanium and zirconium, the weight of the tetravalent titanium compound comprising about 40 to about 60 wt. % of the combined weight of both the tetravalent titanium compound and the tetravalent zirconium compound and, correspondingly, the weight of the tetravalent zirconium compound comprising about 60 to about 40 wt. % of the said combined weight, adding an amount of a hydrolysing agent to said solution sufficient to hydrolyse said titanium compound and said zirconium compound to titania and zirconia, respectively, and to selectively coprecipitate a heterogeneous mixture of titania and zirconia, recovering, washing and pelleting said coprecipitated mixture of titania and zirconia, impregnating said pelleted coprecipitate of titania and zirconia with an organic solution of a soluble phosphorus compound containing phosphorus-oxygen bonds and simultaneously or sequentially draining and heating said impregnated pellets at a temperature of about 200° to about 800° C. for a period of time within the range of about 0.5 to about 5 hours sufficient to thermally chemically bond said 0.5 to 6 wt. % of phosphorus to said pellets in the form of hydroxy-containing phosphate groups.

13. A composition as in claim 12 wherein the tetravalent titanium compound is titanium tetraisopropoxide and the tetravalent zirconium compound is zirconium tetra-n-propoxide.

14. A composition as in claim 13 wherein the hydrolyzing agent is an aqueous solution of isopropanol.

15. A composition as in claim 14 wherein the aqueous solution of isopropanol is an aqueous ammoniacal solution of isopropanol.

16. A method as in claim 17 wherein the soluble phosphorus compound is phosphoric acid.

17. As a new composition of matter, a catalytically active composition consisting essentially of a pelleted mixture of coprecipitated heterogeneous titania and zirconia having about 0.5 to about 6 wt. % of phosphorus thermally chemically bonded to at least the surface thereof in the form of hydroxy-containing phosphate groups, said composition having been prepared by:

preparing a polar organic solvent solution of a tetravalent aliphatic organic compound of titanium and a tetravalent aliphatic organic compound of zirconium, said polar organic solvent solution containing from about 0.5 to about 10 wt. % of said tetravalent compounds of titanium and zirconium, the weight of the tetravalent titanium compound comprising about 40 to about 60 wt. % of the combined weight of both the tetravalent titanium compound and the tetravalent zirconium compound and, correspondingly, the weight of the tetravalent zirconium compound comprising about 60 to about 40 wt. % of the said combined weight, adding an amount of a hydrolysing agent to said solution sufficient to hydrolyse said titanium compound and said zirconium compound to titania and zirconia, respectively, and to selectively coprecipitate a heterogeneous mixture of titania and zirconia, recovering, washing and pelleting said coprecipitated mixture of titania and zirconia, impregnating said pelleted mixture of coprecipitated titania and zirconia with an aqueous solution of a soluble phosphorus compound containing phosphorus-oxygen bonds at a temperature of about 20° to about 150° C., next either draining excess solution from said pellets or heating said impregnated pellets in said solution at a temperature of about 100° to about 150° C. for a period of time within the range of about 0.5 to about 5 hours sufficient to chemically bond said 0.5 to 6 wt. % of phosphorus to said pellets and then stabilizing said pellets by calcination at 200° to about 800° C.

18. A composition as in claim 17 wherein the tetravalent titanium compound is titanium tetraisopropoxide and the tetravalent zirconium compound is zirconium tetra-n-propoxide.

19. A composition as in claim 18 wherein the hydrolyzing agent is an aqueous solution of isopropanol.

20. A composition as in claim 19 wherein the aqueous solution of isopropanol is an aqueous ammoniacal solution of isopropanol.

21. A composition as in claim 20 wherein the soluble phosphorus compound is phosphoric acid.

22. A method for preparing a catalytically active composition consisting essentially of a pelleted heterogeneous coprecipitate of titania and zirconia having about 0.5 to about 6 wt. % of phosphorus thermally chemically bonded thereto in the form of hydroxy-containing phosphate groups, said method comprising the steps of:

a. preparing a polar organic solvent solution of a tetravalent aliphatic organic compound of titanium and a tetravalent aliphatic organic compound of zirconium, said polar organic solvent solution containing from about 0.1 to about 10 wt. % of said tetravalent compounds of titanium and zirconium, the weight of the tetravalent titanium compound comprising about 40 to about 60 wt. % of the combined weight of both the tetravalent titanium compound and the tetravalent zirconium compound and, correspondingly, the weight of the tetravalent zirconium compound comprising about 60 to about 40 wt. % of the said combined weight, b. adding an amount of a hydrolysing agent to said solution sufficient to hydrolyse said titanium compound and said zirconium compound to titania and zirconia, respectively, and to coprecipitate a heterogeneous mixture of titania and zirconia, c. recovering, washing and pelleting said coprecipitated mixture of titania and zirconia, d. impregnating said pellets with a solution of a phosphorus compound containing phosphorus-oxygen bonds over a period of about 0.1 to about 5 hours, e. washing said impregnated pellets, and f. draining and drying said impregnated pellets, g. at least one of said impregnating, washing and drying steps being conducted over a period of at least about 0.5 hours at a temperature within the range of about 200° to about 800° C. sufficient to stabilize said pellets and to thermally chemically bond about 0.5 to 6 wt. % of phosphorus to said pellets in the form of hydroxy-containing phosphate groups.

23. A method as in claim 22 wherein said pellets are impregnated at an ambient temperature of about 20° to about 30° C. and wherein said phosphorus is thermally, chemically bound to said pellets by calcination at a temperature of about 200° to about 800° C. over about a 2 to about a 24 hour period.

24. As a new composition of matter, a catalytically active composition consisting essentially of a pelleted coprecipitated heterogeneous mixture of titania and zirconia having 0.5 to about 6 wt. % of phosphorus thermally chemically bonded thereto in the form of hydroxy-containing phosphate groups, said method consisting essentially of the steps of:

a. preparing a polar organic solvent solution consisting essentially of a tetravalent aliphatic organic compound of titanium and a tetravalent aliphatic organic compound of zirconium, said polar organic solvent solution containing from about 0.1 to about 10 wt. % of said tetravalent compounds of titanium and zirconium, the weight of the tetravalent titanium compound being about 40 to about 60 wt. % of the combined weight of both the tetravalent titanium compound and the tetravalent zirconium compound and, correspondingly, the weight of the tetravalent zirconium compound being about 60 to about 40 wt. % of the said combined weight, b. adding an amount of a hydrolysing agent to said solution sufficient to hydrolyse said titanium compound and said zirconium compound to titania and zirconia, respectively, and to coprecipitate a heterogeneous mixture consisting essentially of titania and zirconia, c. recovering, washing and pelleting said coprecipitated mixture of titania and zirconia, d. impregnating said pellets over a period of about 0.1 to about 5 hours with a solution consisting essentially of a phosphorus compound containing phosphorus-oxygen bonds, e. washing said impregnated pellets, and f. draining and drying said impregnated pellets, g. at least one of said impregnating, washing or drying steps being conducted over a period of about 0.5 to about 24 hours at a temperature within the range of about 200° to about 800° C. sufficient to stabilize said pellets and to thermally chemically bond about 0.5 to 6 wt. % of phosphorus to said pellets in the form of hydroxy-containing phosphate groups.

25. A composition as in claim 24 wherein said pellets are impregnated at an ambient temperature of about 20° to about 30° C. and wherein said phosphorus is thermally, chemically bound to said pellets by calcination at a temperature of about 200° to about 800° C. over about a 2 to about a 24 hour period.

* * * * *